(12) United States Patent
Gumb et al.

(10) Patent No.: US 7,566,321 B2
(45) Date of Patent: Jul. 28, 2009

(54) DEVICE FOR THE INJECTION OF MEDICAL PREPARATIONS WITH CT/MRI MONITORING

(75) Inventors: Lothar Gumb, Graben-Neudorf (DE); Henri Hannula, Eggenstein-Leopoldshafen (DE); Swen Köhn, Karlsruhe (DE); Andreas Melzer, Mühlheim/Ruhr (DE); Aribert Schäf, Bruchsal (DE); Georg Prokott, Eggenstein-Leopoldshafen (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 918 days.

(21) Appl. No.: 10/330,037

(22) Filed: Dec. 26, 2002

(65) Prior Publication Data

US 2003/0171670 A1    Sep. 11, 2003

Related U.S. Application Data

(63) Continuation-in-part of application No. PCT/EP01/06996, filed on Jun. 21, 2001.

(30) Foreign Application Priority Data

Jun. 28, 2000    (DE) ................. 100 30 620

(51) Int. Cl.
| | |
|---|---|
| A61M 5/00 | (2006.01) |
| A61M 37/00 | (2006.01) |
| A61M 5/32 | (2006.01) |
| A61B 5/05 | (2006.01) |
| A61B 6/00 | (2006.01) |

(52) U.S. Cl. .................. 604/191; 604/154; 604/178; 600/420; 600/431; 600/432

(58) Field of Classification Search ............ 604/103.03, 604/117, 174, 175, 151, 154, 155, 156, 191, 604/257, 258, 178; 600/420, 431, 432
See application file for complete search history.

(56) References Cited

U.S. PATENT DOCUMENTS

| | | | | |
|---|---|---|---|---|
| 5,280,427 | A | * | 1/1994 | Magnusson et al. ......... 600/407 |
| 5,469,847 | A | | 11/1995 | Zinreich et al. |
| 5,494,036 | A | * | 2/1996 | Uber et al. .................. 600/432 |
| 5,579,767 | A | * | 12/1996 | Prince ......................... 600/420 |
| 5,997,471 | A | * | 12/1999 | Gumb et al. ................ 600/102 |

(Continued)

FOREIGN PATENT DOCUMENTS

WO    WO 98 23213  A    6/1998

*Primary Examiner*—Kevin C Sirmons
*Assistant Examiner*—Bhisma Mehta
(74) *Attorney, Agent, or Firm*—Klaus J. Bach (57) ABSTRACT

In a device for the injection of medical preparations, into a patients body during an examination in a Computer Tomograph (CT) or in a Magnetic Resonance Tomograph (MRT) or endoscopically, including an injection needle supported by an injection-needle advancing arrangement for insertion of the injection needle into the patients body and the concurrent injection of medications with a separate dosing apparatus, a hose with a check valve for the one-way transport of the medical preparations from the dosing apparatus into the injection needle, as well as a pressure sensor for monitoring the infusion, the injection needle advancing arrangement comprises a needle holder and a linear drive for the movement of the needle holder in parallel with the injection needle and the dosing apparatus has geometric dimensions and consists of materials permitting its insertion into the CT or MRT together with the patient.

5 Claims, 9 Drawing Sheets

U.S. PATENT DOCUMENTS

| | | | |
|---|---|---|---|
| 6,339,718 B1 * | 1/2002 | Zatezalo et al. | 600/432 |
| 6,391,005 B1 * | 5/2002 | Lum et al. | 604/117 |
| 6,508,791 B1 * | 1/2003 | Guerrero | 604/183 |
| 6,565,533 B1 * | 5/2003 | Smith et al. | 604/144 |
| 7,128,729 B2 * | 10/2006 | Duchon et al. | 604/154 |

* cited by examiner

DEVICE FOR THE INJECTION OF MEDICAL PREPARATIONS WITH CT/MRI MONITORING

This is a Continuation-in-Part Application of international patent application PCT/EP01/06996 filed on 21 Jun. 2001 and claiming the priority of German patent application 100 30 620.9 filed 28 Jun. 2000.

BACKGROUND OF THE INVENTION

The invention relates to a device for the injection of medical preparations, particularly medicines or contrast media, into a patients body during an examination in a computer tomograph, CT, magnetic resonance tomograph, MRT, or with an endoscope. The present invention comprises also the use of the apparatus in a magnetic resonance tomograph.

In the interventional radiology, the physician orients and controls his operative actions using imaging procedures such as the CT and MRT. During such a procedure, the patient generally rests on a stretcher, while the physician in charge supervises the procedure on a screen. With tomographic processes such as the CT- and MRT procedures, two-dimensional section images through the patients body, which are taken at small distances, are combined to provide a three-dimensional image, a so-called tomogram, of the patients body. The tomograms generated in this way show the internal organs, the tissue and the bone structures in detail. Any desirable section images can be generated in this way. In addition, individual section representations can be generated with the CT by tilting of the gantry or, with the MRT by a computer program.

Based on the tomographic data, the physician determines his accessing plan for the organ to be subsequently operated on and determines for an image-supported and manipulator-controlled medication administration the coordinates and dosing rates for the insertion of the injection needle and sends the data to the manipulator.

The publication Medrad Medizinische Systeme GmbH; Das Spectris MR-Injektions System, Brochure 1979 of Medrad Inc., USA discloses such a medication dosing system, wherein Medication or contrasting fluid is injected into a patients body by two 65 ml one-way syringes essentially by way of a hose and an injection needle. As it can be assumed from the technical data given, the one-way syringes are operated probably by an electric motor via linear drives. An obvious use of the medication dosing system in an MRT or CT under tomographic control is not mentioned in this publication although the size appears to be suitable for a use in the channel of a tomograph.

A manipulator-controlled medication dosing system, which is suitable for use in a CT or MRT however is not known.

It is the object of the present invention to provide a device for the injection of medical preparations which device is distinct with respect to the prior art in that it can be inserted into a tomograph as a complete unit and can be utilized therein on an imaging basis.

SUMMARY OF THE DISCLOSURE

In a device for the injection of medical preparations, into a patients body during an examination in a Computer Tomograph (CT) or in a Magnetic Resonance Tomograph (MRT) or endoscopically, including an injection needle supported by an injection-needle advancing arrangement for insertion of the injection needle into the patients body and the concurrent injection of medications with a separate dosing apparatus, a hose with a check valve for the one-way transport of the medical preparations from the dosing apparatus into the injection needle, as well as a pressure sensor for monitoring the infusion, the injection needle advancing arrangement comprises a needle holder and a linear drive for the movement of the needle holder in parallel with the injection needle and the dosing apparatus has geometric dimensions and consists of materials permitting its insertion into the CT or MRT together with the patient.

The device according to the invention for the injection of medical preparations will be explained below on the basis of the accompanying drawings showing an embodiment with four one-way syringes.

DESCRIPTION OF PREFERRED EMBODIMENT

Figure 1A:
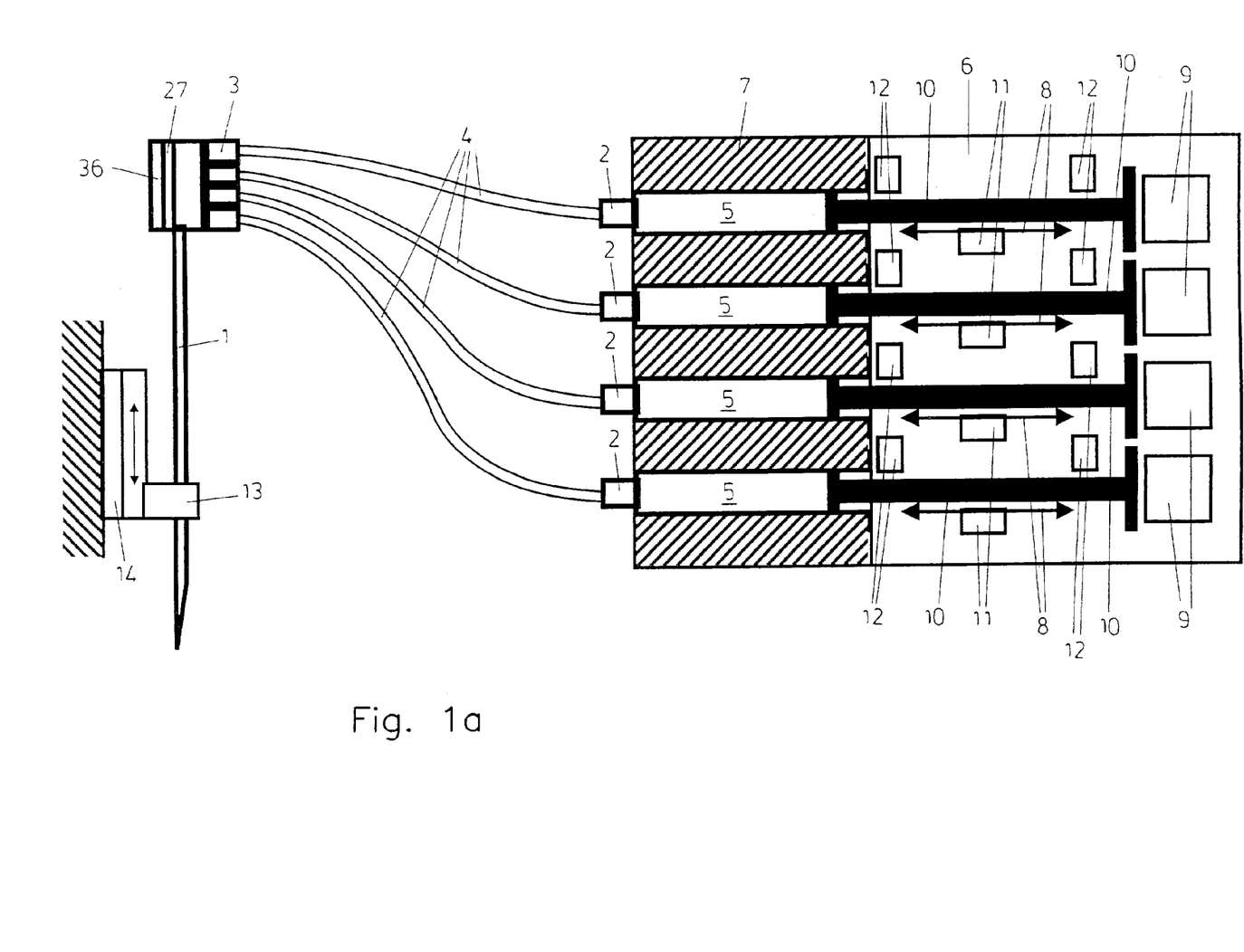
FIG. 1a shows a component of the device for an injection of medical preparations in a schematic representation.
Figure 1B:
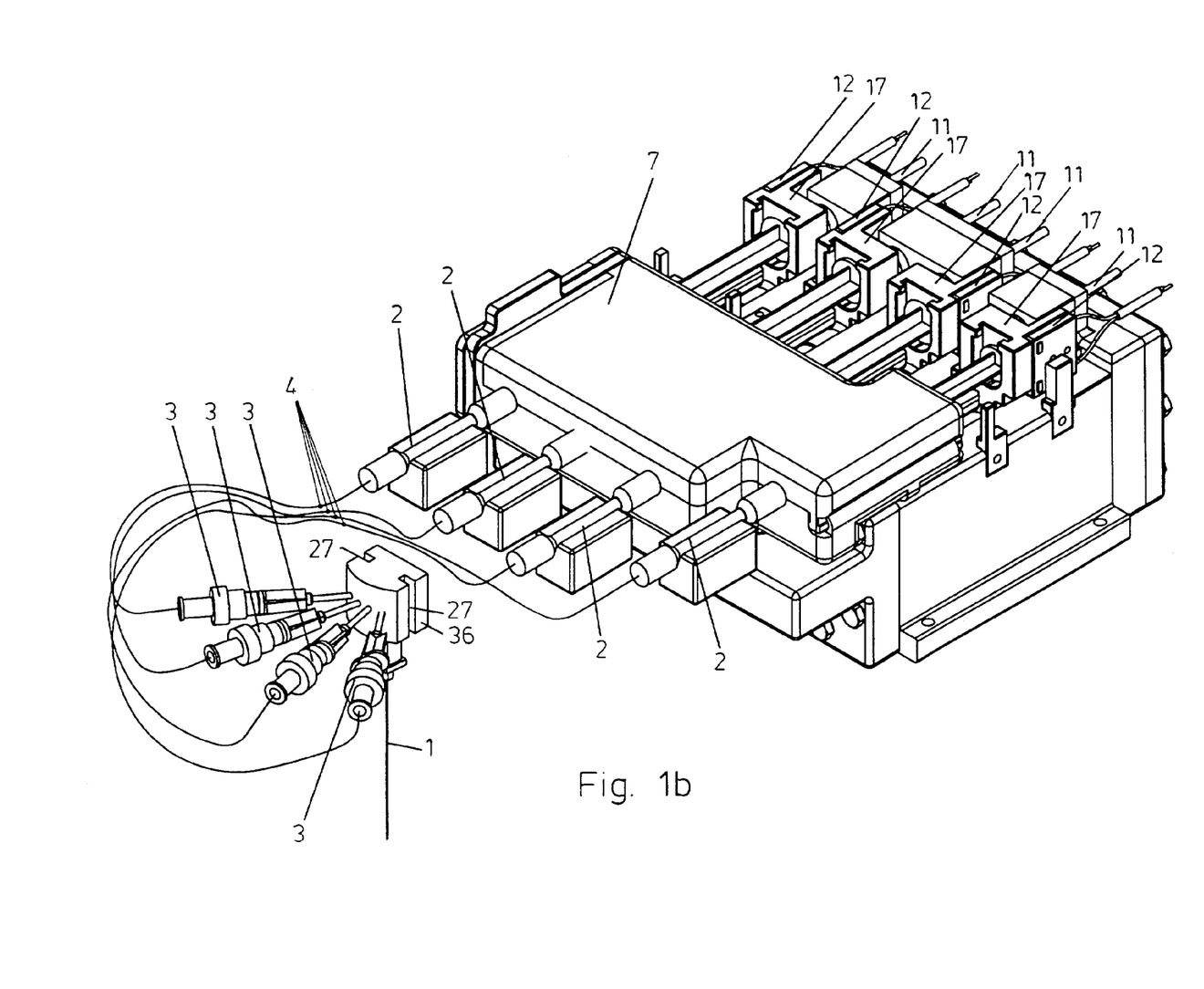
FIG. 1b shows the device according to FIG. 1a in a perspective representation but without the needle holder and the needle moving means.

The embodiment of the device as shown in FIGS. 1a and 1b comprises an infusion needle 1, which is connected to four one-way syringes 5 of a dosing apparatus 6 by way of a mixing chamber 36, four check valves 3, four hoses 4 and four pressure sensors 2. The four one-way syringes 5 are removably disposed in a magazine 7 in the dosing apparatus 6 and are operable each by a drive 9 including a piston 10, which is movable individually for each one-way syringe in both directions 8. However, if a check valve 3 is arranged between the respective one-way syringe 5 and the infusion needle 1, which prevents a return flow, actuation in both direction without reversal or exchange of the check valve 3 is not possible. During operation of a syringe the injection flow is continuously monitored by way of the advance movement of the piston 10 using a travel sensor 11 as well as the pressure measurement by the pressure sensor 2. End switches 12 are provided for limiting the advance movement of the piston 10 in each of its two directions 8 of movement.

In contrast to the schematic representation of FIG. 1a, in the perspective representation of FIG. 1b, the travel sensor 11 is arranged below the piston 10 and moves the pistons 10 by means of a carrier 17 (see also FIG. 2). Furthermore, the travel sensor 11 of the shown embodiment is a linear potentiometer. Alternatively, opto-electronic travel distance measuring procedures can be used in connection with MRTs in an arrangement like that of the travel sensors 11 of FIG. 1b.

Figure 2:
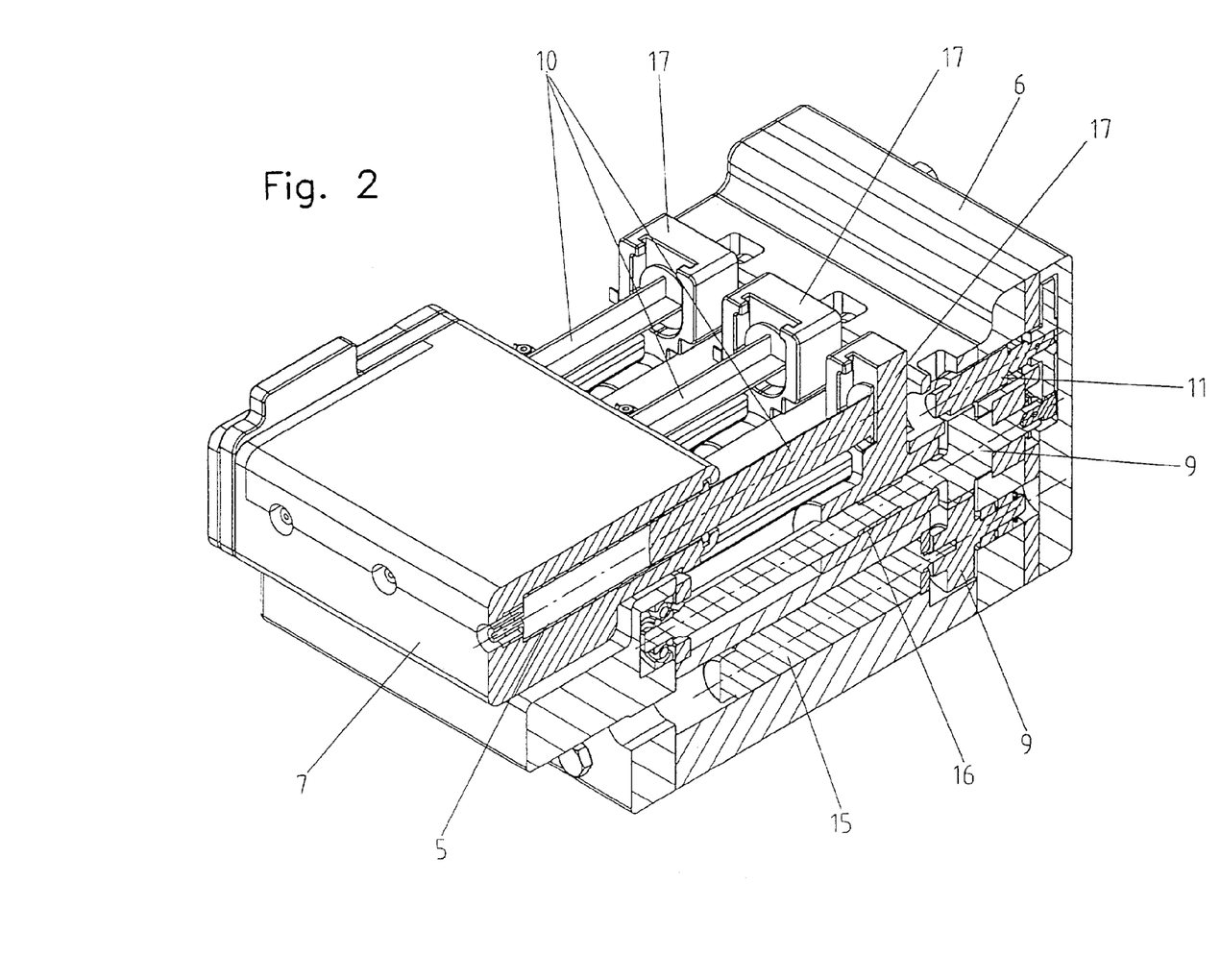
FIG. 2, shows the dosing arrangement 6 according to FIG. 1b in a perspective sectional view.

FIG. 2 shows an embodiment of the dosing apparatus 6 in a perspective cross-sectional representation with a changing magazine 7, the one-way syringes 5 with pistons 10 and the drive 9 of several parts. In the embodiment shown, the drive comprises an electric motor 15, which moves the piston 10 by way of a worm drive 16 with a syringe carrier 17 connected to each syringe piston 10.

If the dosing apparatus 6 is to be used in connection with an MRT, exclusively non-magnetic components can be used for the dosing apparatus in order to avoid magnetic disturbances. To this end, pneumatic or hydraulic turbo drives, one-sided or double-sided operable hydraulic or pneumatic piston drives or, in a limited way, also Kardan-, Bowden cable- or cable drives, which extend to electrical or piezo drives disposed outside the MRT, may be used.

The injection needle 1 is engaged by a reversably operable needle holder 13 as shown in FIG. 1a. The needle holder 13 is supported on an operable displacing device or linear drive 14, which is adjustable axially with the injection needle 1. In this way, the injection needle 1 is movable together with the needle holder 13 over a certain travel distance. If the injection needle 1 is to be further advanced, the needle holder 13 is released and the displacing device 14 is moved back without the injection needle 1 and the needle 1 is then again engaged at a rearward position in order to further advance the needle 1. Depending on the length of the injection needle this procedure can be repeated several times.

The special advantage of this injection needle linear drive or advancing arrangement is its compact design without the need for large piston or linear drives. As a result, the tight space in a channel particularly of an MRT is utilized in an advantageous manner without restriction of the advancing range of the injection needle 1. The system furthermore permits placement of all system components closely to a patient, that is, within a CT or MRT so that the dead volume of the otherwise long medication supply lines is minimized.

Another advantageous of the injection needle advancing arrangement resides in the short exposed length of the needle 1 between the needle holder 13 and the point of insertion into a patient's body even for relatively long needles. The small exposed needle length reduces the chances of the needles, particularly of thin flexible needles, to buckle upon insertion into a body.

Figure 3A:
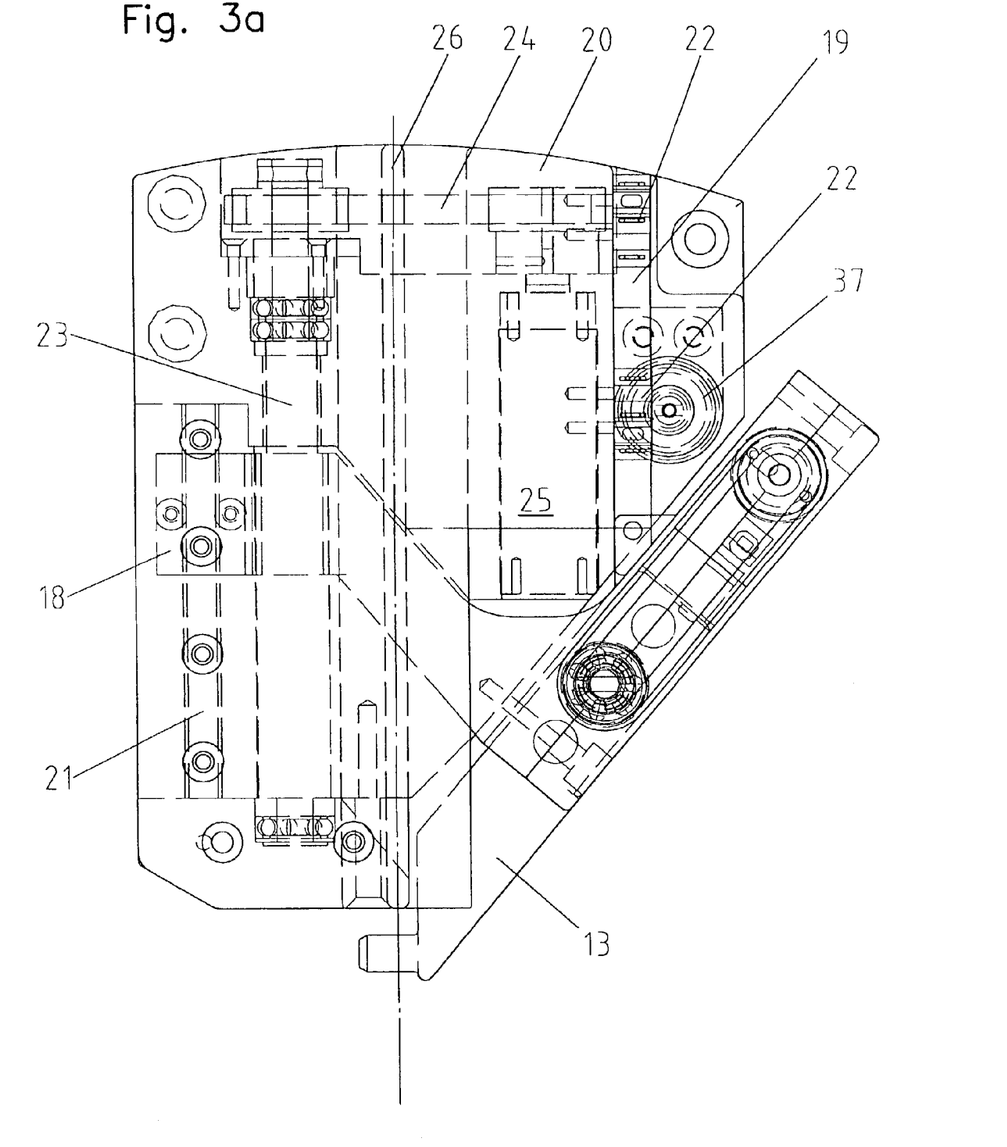
FIGS. 3a and 3b show the injection needle advancing structure without injection needle in a sectional view with different positions of the needle holder.
Figure 3B:
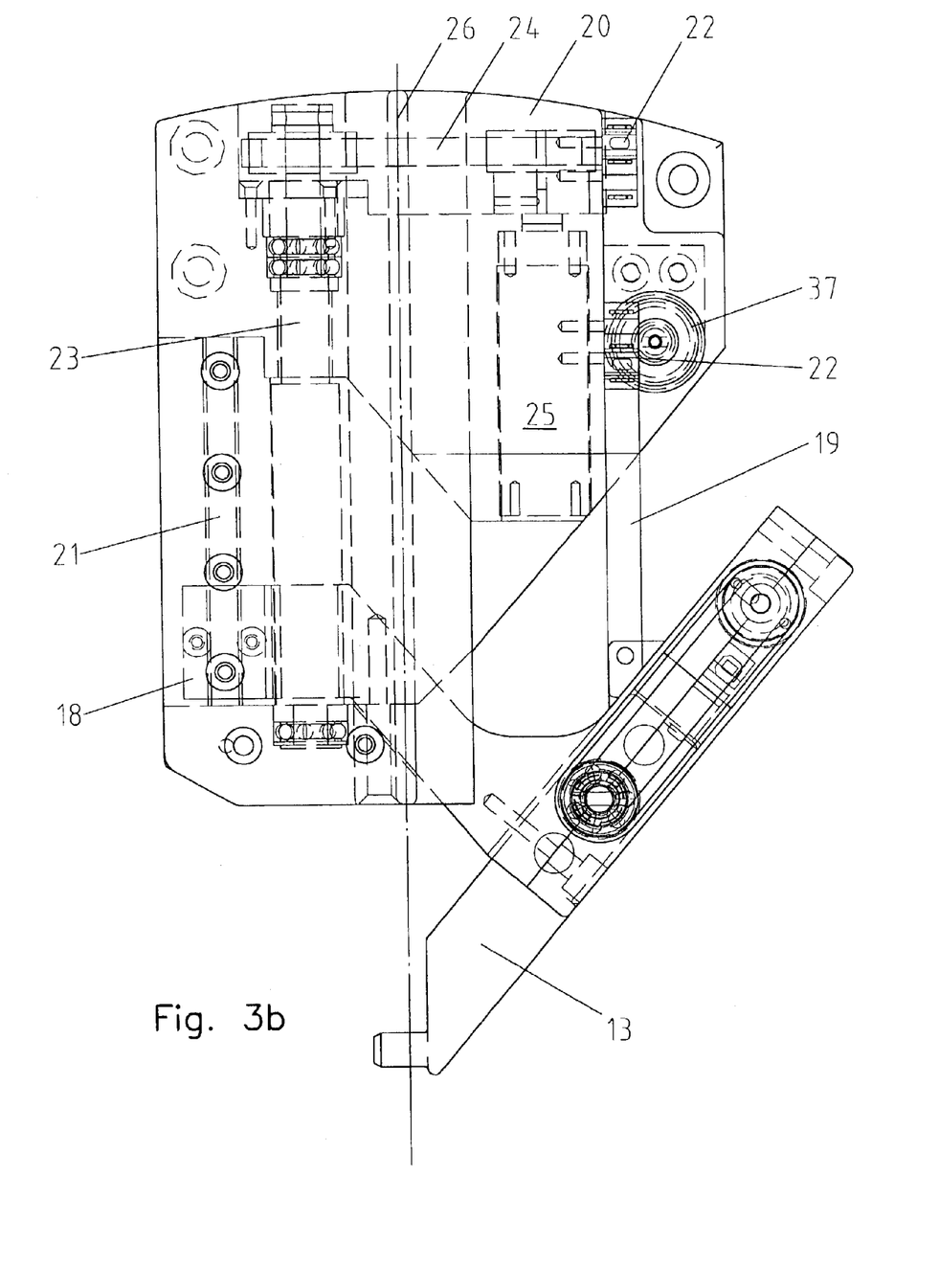
Figure 4A:
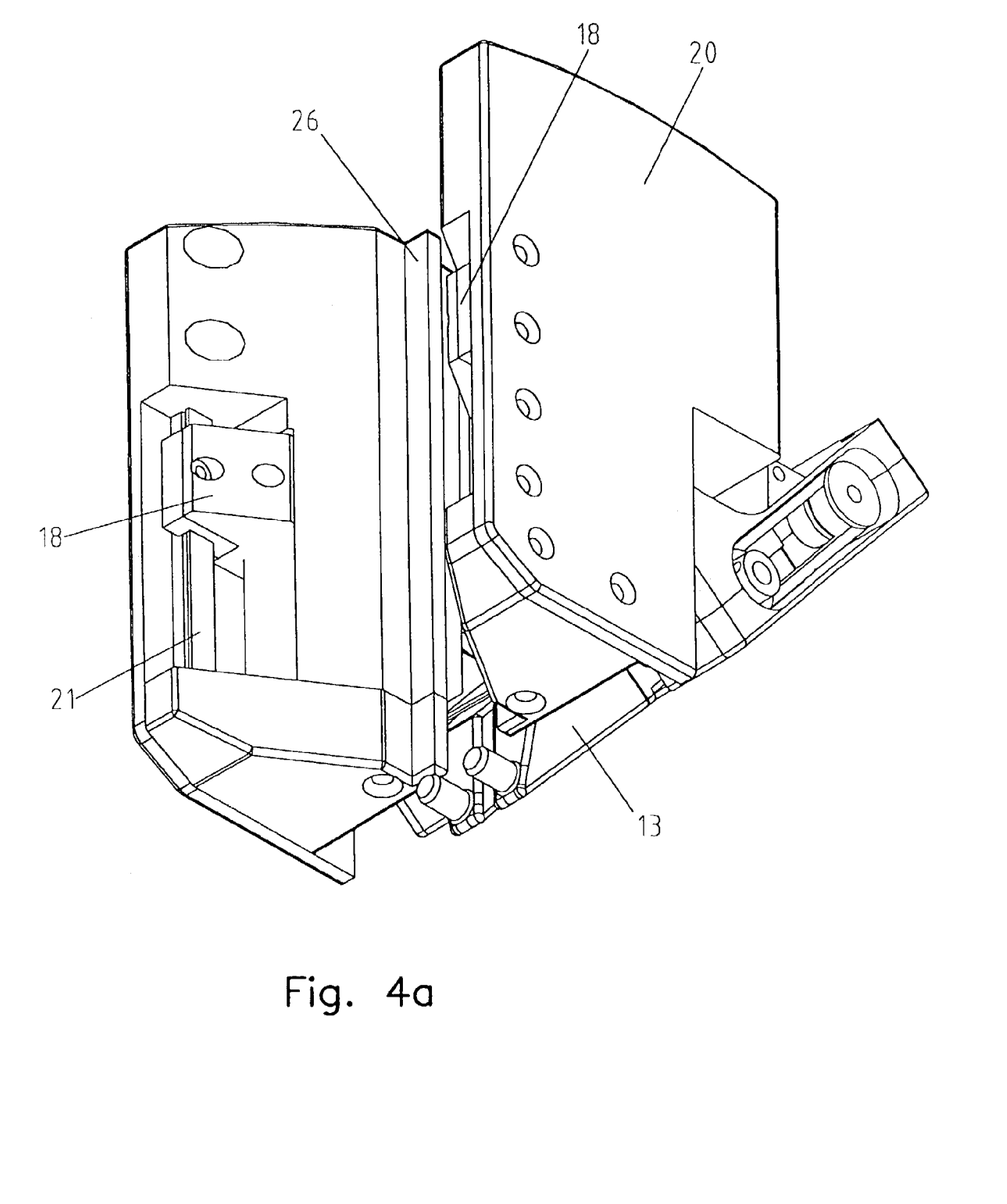
FIGS. 4a and 4b show the injection needle advancing structure in a perspective view with different position of the needle holder.
Figure 4B:
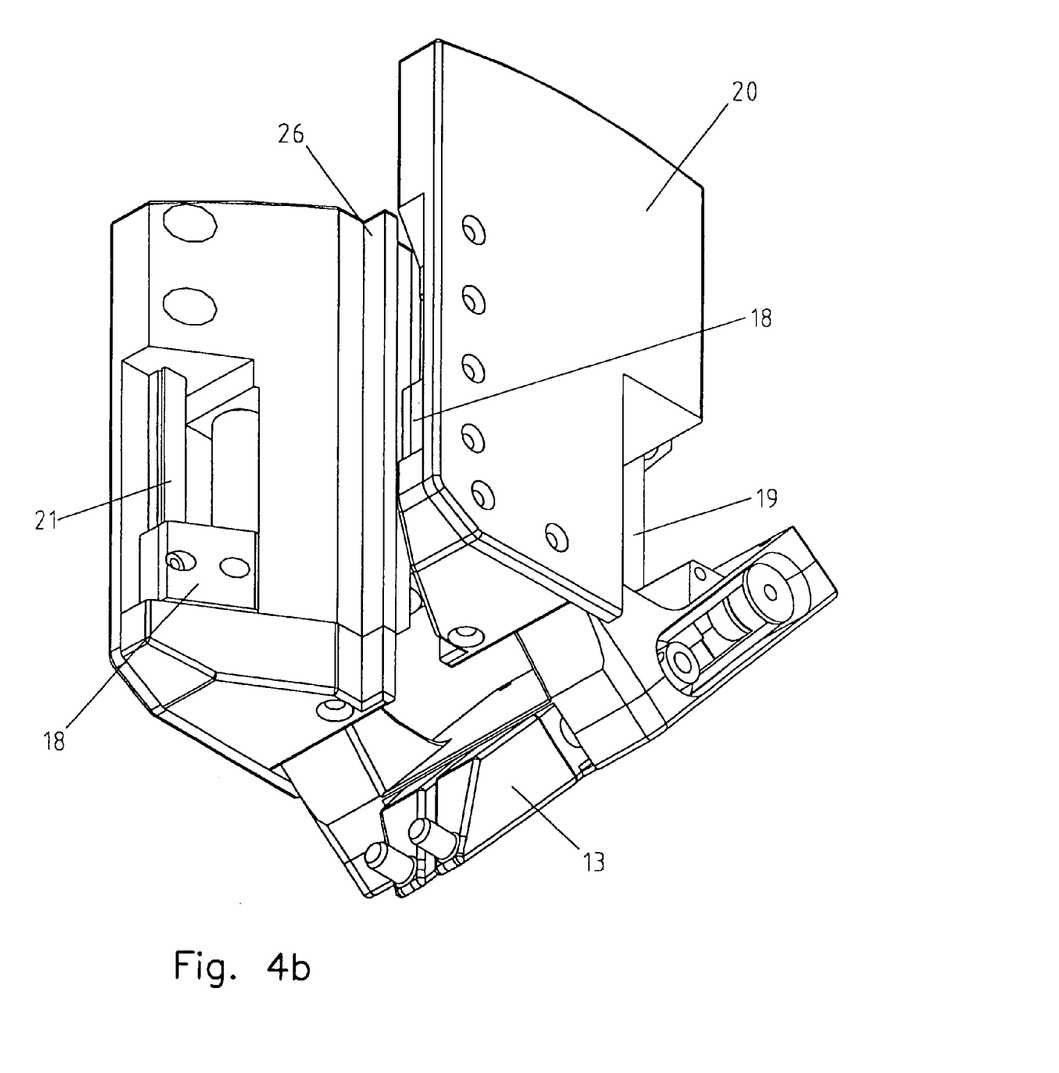

FIGS. 3a and 3b show the injection needle advancing arrangement without injection needle in a sectional view, and FIGS. 4a and 4b show it in a perspective view, wherein the respective "a" designated figures show the needle holder 13 in a retracted position and the "b" designated figures show the needle holder 13 in an advanced position. The displacement device consists of two slide members 18 and a rack 19 which are connected to a needle holder 13 and guided in the housing 20 on two tracks 21 connected to the housing 20 of the needle advancing arrangement as well as a guide structure 22. In the embodiment shown the adjustment movement is achieved by a worm drive 23, which is operated by an electric motor 25 by way of a belt 24.

The position of the needle holder 13 is determined in the embodiment shown by way of a rotary potentiometer 37 with a pinion, which measures the translational movement of the needle holder 13 in the track 21 in the guide structure 22 by way of a rack.

The injection needle is oriented in the housing 20 and guided in the housing 20 in axial direction by guide ledges 26. The mixing chamber 36 shown in FIGS. 1a and 1b serves as holder for the injection needle 1 and the mixing chamber 36 is therefore provided with corresponding guide grooves 27 (see FIG. 1a and 1b). Alternatively, the mixing chamber 36 may be disposed on a separate carrier which, as a separate component, is provided with the necessary guide grooves. In this case, the mixing chamber is releasable from the injection needle advancing arrangement together with the injection needle and the hoses. The housing 20 is open in the area of the guide ledges 26 so that this area is accessible for the insertion of the injection needle into the needle advancing arrangement and also for access to the check valves 3 and the hoses 4 from above, below and from the sides. It furthermore permits the physician to observe the needle insertion procedure.

Figure 5:
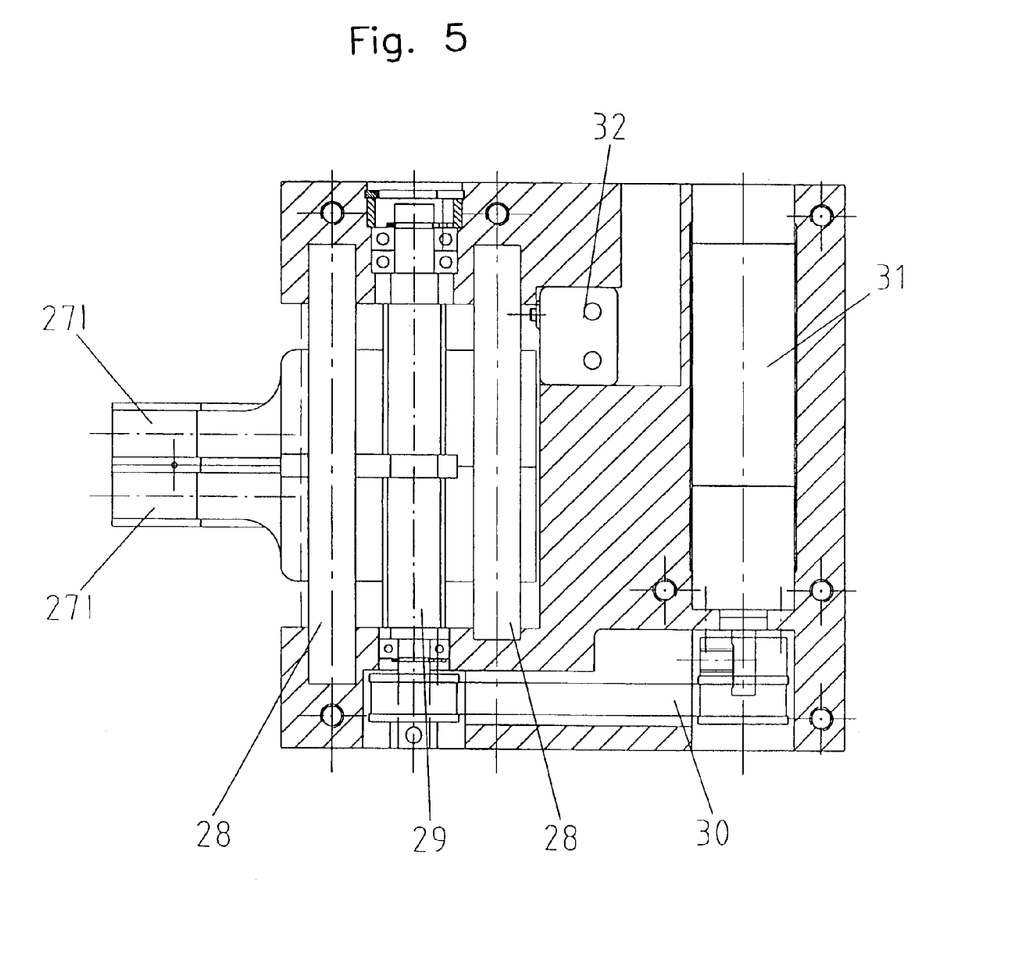
FIG. 5 is a sectional representation of the needle holder.

FIG. 5 shows a section through the needle holder 13. The holder consists mainly of the two jaws 271, which are guided by two guide pins 28 and which are moved in a synchronized motion in opposite directions by a worm drive 29. The worm drive 29 is driven by an electric motor 31 by way of a belt 30, the movement of the jaws 27i away from each other is limited by an end switch 32 for de-energizing the electric motor 31.

For the use of the injection needle advancing structure on a patient in the channel of an MRT exclusively non-magnetic components can be used in order to avoid magnetic disturbances. Consequently, all electric motors must be replaced by pneumatic or hydraulic turbo-drives, piezo drives, single or double-action hydraulic or pneumatic piston drives or, in a limited way, by Kardan- or Bowden cables or cable drives connected to electric motors disposed remote from the MRT.

To facilitate sterilization, the injection needle advancing arrangement can comprise two parts wherein the injection needle 1 and the needle holder 13 are, by design, connected to the first part which can be sterilized and the advancing or displacing device 14 is connected to the second part which is not sterile. The first part is separated from the second part after each procedure and sterilized while another sterilized first part is mounted to the second part so that the device can be used again.

Figure 6:
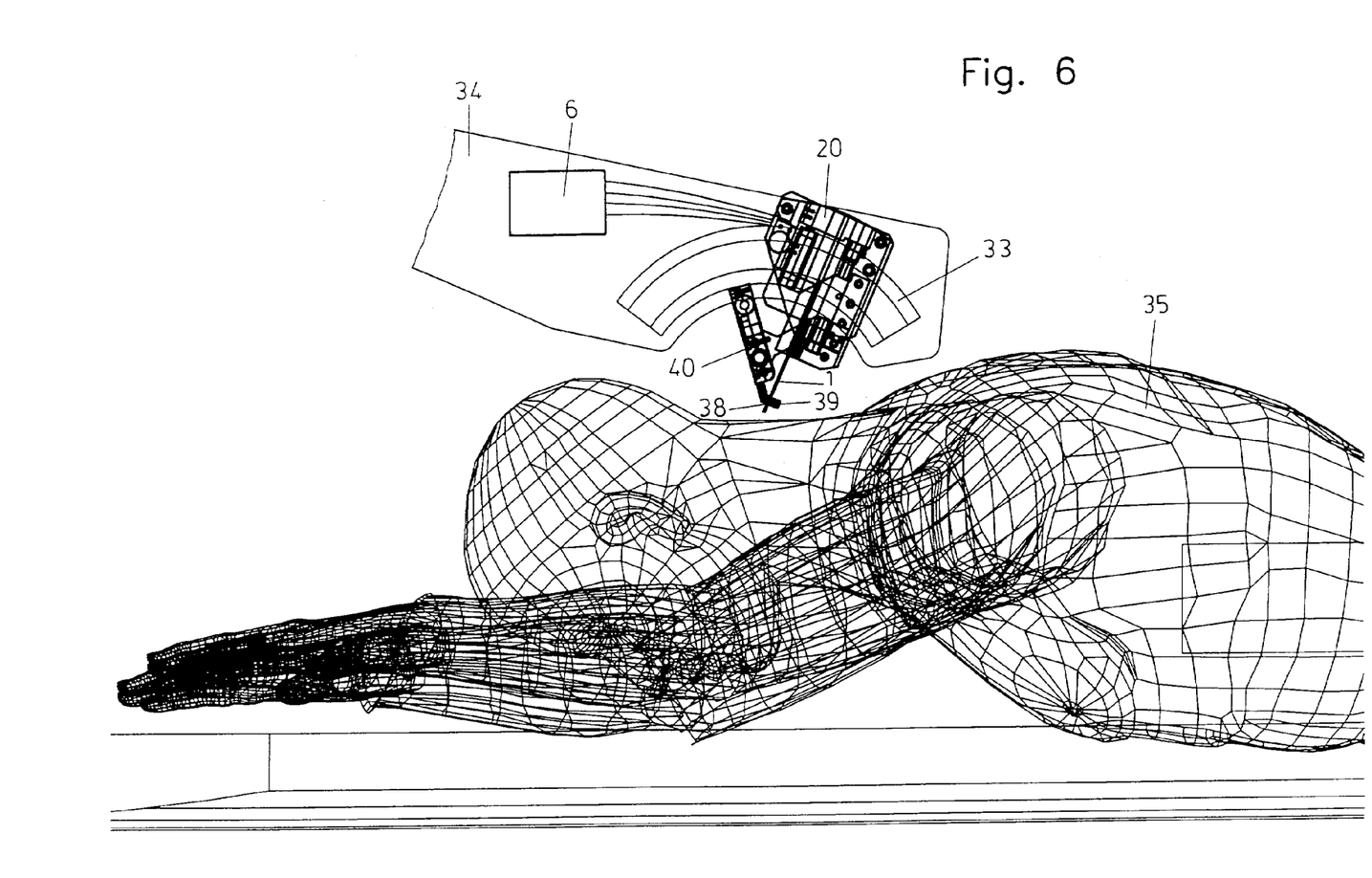
FIG. 6, shows the positioning of the device as determined for an injection of medical preparations on a support above a patient.

For use in the small space available for the device according to the invention in the CT or MRT, the housing 20 of the injection needle advancing arrangement is supported, as shown in FIG. 6, on a C-like curved guide structure 33 according to the state of the art and is movable thereon by a motor and is positioned on a carrier 34, under the control of a manipulator, above a patient 35 resting below. The curved C-shaped guide structure 33 which has a center of curvature connecting with the needle insertion point 38 and the manipulator operated pivot structure for the carrier 34, which is not shown, make it possible to pivot the injection needle advancing arrangement about all spatial degrees of freedom for example about a fixed needle insertion point 38, through which the injection needle can be inserted from various directions. Furthermore, the dosing apparatus 6 may be mounted on the carrier 34 close to the injection needle advancing structure whereby the length of the hoses can be substantially reduced. Short hoses minimize pressure changes and elasticity effects on the medication in the hose and provide therefore for a more accurate dosing of the medications.

Alternatively, the effects of the C-like guide structure 33, that is, the pivoting of the injection needle advancing structure or of another medical instrument can also be achieved by a motor-driven support joint or a rotating table in combination with a computer-based manipulator control.

In addition, a sensor 39 is mounted on the carrier 34 which, by means of a support structure 40 is mounted at the level of the needle insertion point 38 such that the measuring volume is disposed around the needle insertion point on the skin of the patient. The sensor may be for example an annular contact sensor in contact with an annular area around the needle insertion point. In this way, the insertion point 38 can be approached by the needle at an exact surface location for example the surface of the skin of the patient 35. The patient 35 can therefore be prepared by the contact with the sensor 39 on the skin for the expected piercing whereby the chances of the patient twitching upon piercing of the skin are substantially reduced. The sensor 39 consequently monitors the movement of the patient. In addition, or in the alternative, the surface may be marked for recognition by sensors so that it can be recognized by optical detectors, which are not shown, and which can be brought to coincide with the insertion point under manipulator control.

The invention claimed is:

1. A device for the injection of medical preparations into a patients body (35) during an examination in a Computer Tomograph (CT) or in a Magnetic Resonance Tomograph (MRT) or endoscopically, said device including an injection-needle, advancing arrangement, an injection needle (1) supported by said injection-needle advancing arrangement for inserting the injection needle (1) into the body of the patient (35) and the concurrent injection of a medical preparation, a separate dosing apparatus (6) for the storing and sensor controlled transport of the medical preparations, said dosing apparatus (6) including an exchanger magazine (7) for removably accommodating several one-way syringes (5), each including a piston (10), a syringe carrier (17) connected to each syringe and a drive (9) with an electric motor (15) and a worm drive (16) connected to each syringe carrier (17) for independently operating the syringes (5), a separate hose (4) extending from each syringe (5) and being connected to a mixing chamber (36) which is common to all syringes (5) and the hoses (4), each hose including a check valve (3) arranged shortly ahead of the connection to the mixing chamber (36) for the one-way transport of the medical preparations from the dosing apparatus (6) to the injection needle (1) and a pressure sensor (2) in communication with each syringe (5) for monitoring the supply of the medical preparations from the dosing apparatus (6) to the injection needle (1), said injection needle advancing arrangement comprising a needle guide structure, an injection needle holder (13) and an operable linear drive (14) for the movement of the injection needle holder (13) in parallel with the injection needle (1), said injection needle holder linear drive (14) and said dosing apparatus (6) and also the drives (9) thereof having dimensions and consisting of materials permitting the introduction thereof into the CT or MRT and being operative therein, the needle holder (13) is for engaging the needle so as to move the needle (1) together with the needle holder and for releasing the needle so as to move the needle holder without moving the needle for repositioning the holder on the needle.

2. Device according to claim 1, wherein all components of the device consist of a non-magnetic material, and neither the syringe carrier drives (9) nor the linear drive (14) of the device furthermore requires or generates a magnetic or electrical field but is a pneumatic or hydraulic drive or a piezo drive, any magnetically generated drive power being generated outside the CT or MRT, the drive power being then transmitted to the device mechanically by way of Kardan- Bowden cable- or cable drives or hydraulically or pneumatically by pressure piston drives.

3. Device according to claim 1, wherein the injection needle (1) is movable by pivoting arrangements including a curved guide structure (33) having a center of curvature coinciding with a needle insertion point (38).

4. Device according to claim 3, wherein the device includes a sensor (39) which operates pneumatically or hydraulically or optoelectronically and which is arranged at the level of the needle insertion point (38) for sensing any movement of the patient.

5. Device according to claim 1, wherein the injection needle advancing arrangement is a two-part modular design, and the injection needle (1) and the needle holder (13) are associated with a first part which can be sterilized and the linear drive (14) for moving the needle is associated with a second part which does not need to be sterile.

* * * * *